United States Patent
Wu et al.

(10) Patent No.: US 10,149,647 B2
(45) Date of Patent: Dec. 11, 2018

(54) WEANING READINESS INDICATOR, SLEEPING STATUS RECORDING DEVICE, AND AIR PROVIDING SYSTEM APPLYING NONLINEAR TIME-FREQUENCY ANALYSIS

(71) Applicant: PhyzQ Research Inc., Grand Cayman (KY)

(72) Inventors: Hau-Tieng Wu, Toronto (CA); Chun-Hung Chen, Hsinchu County (TW); Sam Hong-Yi Huang, Palo Alto, CA (US); Yu-Lun Lo, Taipei (TW)

(73) Assignee: PHYZQ RESEARCH INC., Grand Cayman (KY)

( * ) Notice: Subject to any disclaimer, the term of this patent is extended or adjusted under 35 U.S.C. 154(b) by 223 days.

(21) Appl. No.: 14/906,949

(22) PCT Filed: Oct. 8, 2015

(86) PCT No.: PCT/US2015/054722
§ 371 (c)(1),
(2) Date: Jan. 22, 2016

(87) PCT Pub. No.: WO2016/057806
PCT Pub. Date: Apr. 14, 2016

(65) Prior Publication Data
US 2016/0228051 A1    Aug. 11, 2016

Related U.S. Application Data

(60) Provisional application No. 62/061,145, filed on Oct. 8, 2014.

(51) Int. Cl.
*A61B 5/0205*    (2006.01)
*A61B 5/0456*    (2006.01)
(Continued)

(52) U.S. Cl.
CPC .......... *A61B 5/4806* (2013.01); *A61B 5/0205* (2013.01); *A61B 5/0456* (2013.01);
(Continued)

(58) Field of Classification Search
CPC . A61B 5/4806; A61B 5/0205; A61B 5/04012; A61B 5/0456; A61B 5/08;
(Continued)

(56) References Cited

U.S. PATENT DOCUMENTS 8,801,619 B2 *   8/2014   Baker, Jr. ........... A61B 5/02405
                                                          128/204.23
8,882,684 B2 *   11/2014  Halperin ............... A61B 5/002
                                                             600/300

(Continued)

OTHER PUBLICATIONS

International Search Report (PCT/ISA/210) issued in PCT/US2015/054722 dated Jan. 4, 2016 (2 pgs.).
(Continued)

*Primary Examiner* — Navin Natnithithadha
(74) *Attorney, Agent, or Firm* — Muncy, Geissler, Olds & Lowe, P.C.

(57) ABSTRACT

A weaning readiness indicator is disclosed. The weaning readiness indicator includes a monitor, a memory, a processor, and a display. The monitor monitors a ventilated patient for a predetermined time length and generates a respiratory signal. The memory stores an algorithm, where the algorithm includes performing a nonlinear time frequency analysis on the respiratory signal to obtain a time frequency representation function, extracting one or more features from the time frequency representation function, and computing a weaning readiness index based on the one or more features. The processor is connected to the monitor and the memory, and executes the algorithm. The display is connected to the processor and provides an indication of the weaning readiness index of the ventilated patient. A sleeping
(Continued)

status recording device and an air providing system applying nonlinear time frequency analysis are also disclosed.

5 Claims, 5 Drawing Sheets

(51) Int. Cl.
*A61B 5/087* (2006.01)
*A61B 5/08* (2006.01)
*A61B 5/00* (2006.01)
*A61M 16/00* (2006.01)
*A61B 5/04* (2006.01)

(52) U.S. Cl.
CPC ............... *A61B 5/08* (2013.01); *A61B 5/087* (2013.01); *A61B 5/4815* (2013.01); *A61B 5/7253* (2013.01); *A61B 5/742* (2013.01); *A61M 16/0003* (2014.02); *A61M 16/0051* (2013.01); *A61M 16/026* (2017.08); *A61B 5/04012* (2013.01); *A61B 5/4812* (2013.01); *A61B 5/4836* (2013.01); *A61B 5/726* (2013.01); *A61B 5/7257* (2013.01); *A61M 2205/3327* (2013.01); *A61M 2205/502* (2013.01); *A61M 2230/04* (2013.01); *A61M 2230/06* (2013.01); *A61M 2230/42* (2013.01)

(58) Field of Classification Search
CPC ..... A61B 5/087; A61B 5/4815; A61B 5/7253; A61B 5/7257; A61B 5/726; A61B 5/742; A61B 5/4812; A61M 16/0003; A61M 16/0051; A61M 2205/3327; A61M 2205/502; A61M 2230/04; A61M 2230/06; A61M 2230/42

USPC ........................................ 600/484, 529–543
See application file for complete search history.

(56) References Cited

U.S. PATENT DOCUMENTS

| | | | |
|---|---|---|---|
| 8,998,830 B2* | 4/2015 | Halperin | A61B 5/002 600/300 |
| 2001/0014776 A1 | 8/2001 | Oriol et al. | |
| 2005/0267362 A1 | 12/2005 | Mietus et al. | |
| 2006/0235315 A1 | 10/2006 | Akselrod et al. | |
| 2010/0307499 A1 | 12/2010 | Eger et al. | |
| 2012/0041279 A1* | 2/2012 | Freeman | A61B 5/0205 600/301 |
| 2013/0006075 A1 | 1/2013 | Baker, Jr. et al. | |
| 2013/0267791 A1* | 10/2013 | Halperin | A61B 5/002 600/300 |
| 2014/0005502 A1* | 1/2014 | Klap | A61B 5/0205 600/301 |
| 2014/0235959 A1 | 8/2014 | Jafari et al. | |
| 2014/0350351 A1* | 11/2014 | Halperin | A61B 5/002 600/300 |

OTHER PUBLICATIONS

Written Opinion of the International Search Authority (PCT/ISA/237) issued in PCT/US2015/054722 dated Jan. 4, 2016 (7 pgs.).
Wu et al., "Evaluating physiological dynamics via Synchrosqueezing: Prediction of ventilator weaning", Journal of Latex Class Files, vol. 11, No. 4, Dec. 2012. ( 9 pp.) Retrieved on [Nov. 23, 2015], retrieved from the internet <URL: https://web.math.princeton.edu/~hauwu/WuHseuBienKouDaubechies2012.pdf>.

* cited by examiner

WEANING READINESS INDICATOR, SLEEPING STATUS RECORDING DEVICE, AND AIR PROVIDING SYSTEM APPLYING NONLINEAR TIME-FREQUENCY ANALYSIS

CROSS-REFERENCE TO RELATED APPLICATION

This application claims the benefit of U.S. Provisional Application No. 62/061,145, filed on Oct. 8, 2014, in the United States Patent and Trademark Office, the disclosure of which is incorporated herein in their entirety by reference.

BACKGROUND OF THE INVENTION

1. Field of the Invention

This application relates to a weaning readiness indicator, a sleeping status recording device, and an air providing system, and more particularly, to a weaning readiness indicator, a sleeping status recording device, and an air providing system applying nonlinear time-frequency analysis (NTFA).

2. Description of the Related Art

In medical procedures for treating a patient's health issue, the first step is to obtain the biological data of the patient. In addition to the general information such as height, age, or gender, the most common examinations are blood test, imaging information, nerve conduction examination, etc., which include invasive and non-invasive examinations. Each examination has its different values and necessities under different circumstances and different timings. In recent decades, the dynamic information of physiological signals, such as heart rate variability (HRV) and breathing rate variability (BRV), have become a study of interest. Many doctors and researchers are keen on understanding the dynamic information of physiological signals to further improve medical treatments.

Since the invasive examination is not conducive for the long time data collection, we are focusing on the non-invasive examinations first before the invention of the simplified invasive examinations. The common non-invasive examinations include electrocardiography (ECG), respiratory signals, medical imaging, etc. However, medical imaging requires a high cost, and is limited to describe the dynamic variation over a short period of time. On the other hand, some data such as time-varying frequency and amplitude of the ECG signals or the respiratory signals are important subjects of great interests to many scientists. According to the recent researches, the HRV and the BRV may contain a lot of precious physiological information. However, even with lots of efforts over many years, the clinical values of such signals are still limited.

Examples of dynamical information with clinical value extracted from the physiological signal include time-varying frequency and amplitude. In general, such time-varying frequency is not measured directly, but is inferred from the temporally oscillatory signals. A well-known example is the analysis of R-peak to R-peak intervals (RRI) to reveal HRV information. To study the extracted time-very frequency signal, many techniques are introduced, including, for example, spectral method and nonlinear dynamical analysis, such as Poincare map, entropy analysis, fractal analysis.

However, there are some of the following limitations with these established analysis techniques. Firstly, a relatively large number of oscillations must be observed in the physiologic signal. For example, when applying Poincare map or approximate entropy analysis on the respiratory signal, at least 300 and 100 to 1000 oscillations are needed respectively. Second of all, it is not always straightforward to determine the oscillation-to-oscillation time series from the given physiological signals, as there is no reliable determination of the "true" landmarks that can be guaranteed. Furthermore, in some cases, it is even hard to provide a universally accepted definition of a landmark (e.g., ECG signals). Third, the information will be over-reduced inside the physiological signal if what is retained is only the oscillation-to-oscillation time series.

SUMMARY OF THE INVENTION

By utilizing novel mathematical tools with a rigorous theory backup, a breakthrough improvement of the physiological signal analysis is achieved in recent years. This improvement can be summarized in a series of process. First, the objectives and properties of data analysis are systematically analyzed to build an essential mathematical model. Sequentially, various algorithms are provided in order to extract important parameters from the signals for the essential mathematical model. Finally, by using appropriate concept of machine learning, those extracted parameters can be converted into clinic usable parameters. The resulted parameters from the described process are termed as "dynamic physiological parameters". The resulted dynamic physiological parameters can directly correspond to the traditional laboratory parameters from common clinic methods. For example, in the blood test, the blood sample may be the analyzed signal, the hematology analyzer may be the data analysis tool, and the blood parameter (e.g., the number of red and white blood cells) may be the dynamic physiological parameter. Through the clinical verification, the correlation between the dynamic physiological parameters and the clinical procedures can be easily understood. For example, if the dynamic physiologic parameter is abnormal, it may indicate that the patient may have some issues. The described process is realized in the respiratory signal analysis. A series of exploits and developments relating to the described process are made in the applications such as ventilator weaning, sleeping status indication, and anesthesia.

In order to overcome the limitations of the traditional techniques for the sake of extracting physiological dynamics, nonlinear time frequency analysis (NTFA) techniques, like synchrosqueezing transform (SST) and its variations are considered in the present invention to obtain the dynamical features of a given physiological signal. The features extracted from the respiratory signal via NTFA are shown to be practical, meaningful and intimately related to the underlying dynamics. The extracted features are successfully applied to various fields where respiratory signals provide essential information. Hereinafter, the application of NTFA, in particular SST, will be described in detail.

According to one objective of the present invention, a weaning readiness indicator is provided. The weaning readiness indicator includes a monitor, a memory, a processor, and a display. The monitor monitors a ventilated patient for a predetermined time length and generates a respiratory signal. The memory stores an algorithm, where the algorithm includes performing a nonlinear time frequency analysis (NTFA) on the respiratory signal to obtain a time frequency representation (TFR) function, extracting one or more features from the TFR function, and computing a weaning readiness index based on the one or more features. The processor is connected to the monitor and the memory, and executes the algorithm. The display is connected to the processor and provides an indication of the weaning readiness index of the ventilated patient.

Preferably, the features may include an instantaneous frequency, an amplitude modulation and a time varying shape index.

Preferably, in the algorithm, the step of performing the NTFA on the respiratory signal to obtain the TFR function may include performing a linear time frequency transform on the respiratory signal to obtain a linear time frequency transformed function, calculating a reallocation rule from the linear time frequency transformed function, and reallocating coefficients of the linear time frequency transformed function based on the reallocation rule to obtain the TFR function based on NTFA.

Preferably, the instantaneous frequency, the amplitude modulation and the time varying shape index may be generated by a casual reassignment method.

Preferably, the linear time frequency transform may include a short time Fourier transform (STFT) and a continuous wavelet transform (CWT).

Preferably, the predetermined time length may be less than 5 minutes.

Preferably, the monitor may include a pneumotachometer, a turbine pneumotach, or an ultrasonic spirometer.

According to another objective of the present invention, a sleeping status recording device is provided. The sleeping status recording device includes a monitor, an algorithm memory, a processor, and a storage memory. The monitor monitors a sleeping patient and generating a respiratory signal and an electrocardiography (ECG) signal. The algorithm memory stores an algorithm, where the algorithm includes performing a nonlinear time frequency analysis (NTFA) on the respiratory signal and an R-peak to R-peak interval (RRI) signal extracted from the ECG signal to obtain time frequency representation (TFR) functions respectively, extracting one or more features from the TFR functions, and determining a sleeping status based on the one or more features. The processor is connected to the monitor and the algorithm memory and executes the algorithm to obtain the sleeping status. The storage memory is connected to the processor and stores the sleeping status.

Preferably, the features may include an instantaneous frequency, an amplitude modulation and a coupling index.

Preferably, in the algorithm, the step of performing the NTFA on the respiratory signal and the RRI signal to obtain the TFR functions may include performing a linear time frequency transform on the respiratory signal and the RRI signal to obtain a linear time frequency transformed function, calculating a reallocation rule from the linear time frequency transformed function, and reallocating coefficients of the linear time frequency transformed function based on the reallocation rule to obtain the TFR functions associated with the NTFA.

Preferably, the linear time frequency transform may include a short time Fourier transform (STFT) and a continuous wavelet transform (CWT).

Preferably, the monitor may include an ECG machine, a pneumotachometer, a turbine pneumotach, an ultrasonic spirometer, a magnetometer, or a strain gauge.

According to another objective of the present invention, an air providing system is provided. The air providing system includes a monitor, a memory, a processor, and a ventilator. The monitor monitors a patient for a predetermined time length and generates a respiratory signal. The memory stores an algorithm, where the algorithm includes performing a nonlinear time frequency analysis (NTFA) on the respiratory signal to obtain a time frequency representation (TFR) function, extracting one or more features from the TFR function, and computing a respiratory state indication of the patient based on the one or more features. The processor is connected to the monitor and the memory, and executes the algorithm. The ventilator is connected to the processor and provides air to the patient according to the respiratory state indication.

Preferably, the features may include an instantaneous frequency, an amplitude modulation and a time varying shape index.

Preferably, in the algorithm, the step of performing the NTFA on the respiratory signal to obtain the TFR function may further include performing a linear time frequency transform on the respiratory signal to obtain a linear time frequency transformed function, calculating a reallocation rule from the linear time frequency transformed function, and reallocating coefficients of the linear time frequency transformed function based on the reallocation rule to obtain the TFR function associated with the chosen NTFA.

Preferably, the linear time frequency transform may include a short time Fourier transform (STFT) and a continuous wavelet transform (CWT).

Preferably, the monitor may be disposed in the ventilator.

Preferably, the monitor may include a pneumotachometer, a turbine pneumotach, or an ultrasonic spirometer.

Preferably, the ventilator may adjust pressure or oxygen concentration of the air by a software program, and the respiratory state indication may be one of the parameters of the software program.

As mentioned above, the weaning readiness indicator, the sleeping status recording device, and the air providing system in accordance with the present invention may have one or more advantages as follows.

1. The weaning readiness indicator, the sleeping status recording device, and the air providing system with the present invention is able to achieve high accuracy compared to the traditional clinical methods.

2. The weaning readiness indicator, the sleeping status recording device, and the air providing system with the present invention is able to extract important features from the physiologic signals in relatively shorter time interval due to the property of NTFA.

3. The weaning readiness indicator, the sleeping status recording device, and the air providing system with the present invention is able to determine relatively more precise status of the patent from the physiologic signals which show non-significant patterns.

BRIEF DESCRIPTION OF THE DRAWINGS

The exemplary embodiment(s) of the present invention will be understood more fully from the detailed description given below and from the accompanying drawings of various embodiments of the invention, which, however, should not be taken to limit the invention to the specific embodiments, but are for explanation and understanding only.

DETAILED DESCRIPTION OF THE PREFERRED EMBODIMENTS

Hereinafter, embodiments of the present invention will be described in detail with reference to the accompanying drawings so that those skilled in the art to which the present invention pertains can realize the present invention. As those skilled in the art would realize, the described embodiments may be modified in various different ways, all without departing from the spirit or scope of the present invention.

Figure 1:
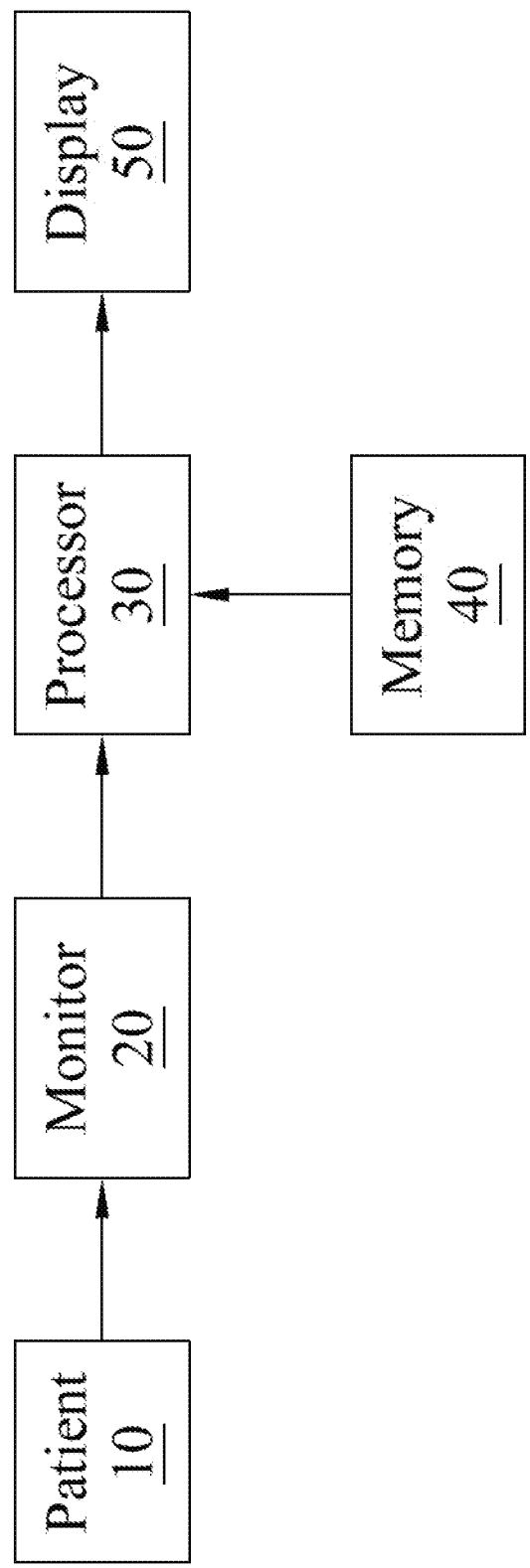
FIG. 1 illustrates a schematic diagram of a weaning readiness indicator in accordance with a first embodiment of the present invention.

Please refer to FIG. 1, which is a schematic diagram of a weaning readiness indicator in accordance with a first embodiment of the present invention. In FIG. 1, the weaning readiness indicator includes a monitor 20, a memory 40, a processor 30, and a display 50. The monitor 20 monitors a ventilated patient 10 for a predetermined time length and generates a respiratory signal. The memory 40 stores an algorithm, where the algorithm includes performing a NTFA on the respiratory signal to obtain a TFR function, extracting one or more features from the TFR function, and computing a weaning readiness index based on the one or more features. The processor 30 is connected to the monitor 20 and the memory 40, and executes the algorithm. The display 50 is connected to the processor 30 and provides an indication of the weaning readiness index of the ventilated patient.

Making a weaning decision for a ventilated patient is an important clinical issue. Since extended intubation has many negative side effects, such as an increased risk for infection, physicians seek to extubate as soon as medically possible. However, weaning too early may lead to re-intubation, and thus the patents may be subject to extra stress or higher mortality rate. Therefore, it is important to accurately decide when the patients can be weaned from the ventilators.

To further increase the weaning success possibility, the weaning readiness indicator of the embodiment of the present invention applies NTFA to analyze the respiratory signal obtained from the patient 10. In particular, the monitor 20 can monitor the air flow generated by the patient's breathing, and send the obtained respiratory signal to the processor 30. In the meantime, the processor 30 loads the algorithm applying NTFA from the memory 40, and then performs the algorithm on the received respiratory signal to obtain a value as the weaning readiness index. The weaning readiness index is sent to and shown on the display 50, so the physician can easily evaluate the weaning readiness for the patient 10 according to the provided weaning readiness index. Compared to the commonly used parameter, such as rapid shallow breathing index (RSBI), the weaning readiness index obtained from NTFA can provide higher accuracy. In addition, due to the property of NTFA, only short oscillation-to-oscillation time interval is required to provide the result.

Preferably, the features may include an instantaneous frequency and an amplitude modulation. In the algorithm, the step of performing a NTFA on the respiratory signal to obtain a TFR function may include performing a linear time frequency transform on the respiratory signal to obtain a linear time frequency transformed function, calculating a reallocation rule from the linear time frequency transformed function, and reallocating coefficients of the linear time frequency transformed function based on the reallocation rule to obtain the TFR function.

Hereinafter, the algorithm used in the embodiment of the present invention will be described in detail. The following description applied to other oscillatory physiological signals, but the respiratory signal is chosen as an illustration. The respiratory signal is denoted as R(t). To quantify its dynamical behavior, the respiratory signal can be model as an amplitude modulation and frequency modulation (AM-FM) signal:

$$R(t) = A(t)s(\phi(t)) \tag{1}$$

where $s(\cdot)$ is a continuously differentiable periodic function designated as the wave shape function, and $s(t) = s(t+2\pi)$ for all t, where $s(\cdot)$ is an oscillating function that satisfies mild technical conditions. The derivative $\phi'(t)$ of the phase function $\phi(t)$ is called as the instantaneous frequency (IF) of the respiratory signal and A(t) is called the amplitude modulation (AM) of the respiratory signal.

A(t) and $\phi'(t)$ are required to be positive. Furthermore, if over a period I of length T>0, the variation of $\phi'(t)$ and A(t) are slight from tone period to the next. That is, $|\phi''(t)| \leq \epsilon \phi'(t)$, and $|A'(t)| \leq \epsilon \phi'(t)$ for all $t \in I$. In that case, the signal is defined as rhythmic over I; otherwise, the signal is nonrhythmic.

Subsequently, R(t) can be discretized with the sampling period $\tau > 0$ from time 0 to time L>0. The digitalized signal is denoted as $x \in \mathbb{R}^N$, where $N = [L/\tau]$.

In reality, the digitalized signal x is contaminated by noise or measurement error and thus the deviated respiratory signal can be modeled as:

$$y_i = x_i + \sigma_i \Phi_i \tag{2}$$

where $i = 1, \ldots, N$, $\Phi_i$ is the noise with variance 1, which is possibly time dependent, and $\sigma_i > 0$ for all i satisfying $|\sigma_i - \sigma_{i+1}| \leq \epsilon$. Although the possible noise appearing in the medical process is versatile, the model provided in this embodiment covers a large portion of it. For example, the autoregressive and moving averaged noise and ever "slightly" non-stationary noise are covered. It is worth noting that the commonly used Gaussian white noise model is when $\sigma_i = 1$ and $\Phi i$ is an independent and identically distributed (i.i.d.) Gaussian random variables.

Next, different NTFA techniques are applied to analyze $y_i$. There are three main steps in NTFA in this embodiment.

Step 1. A chosen linear time frequency analysis technique is implemented. In this embodiment, continuous wavelet transform (CWT) is used as an illustrative example. However, the present invention is not limited thereto. For example, short time Fourier transform (STFT) can be used. Take the scales $a_j = 2^{j/nv} \tau$, $j = 1, \ldots, Lnv$, where nv is the "voice number" chosen by the user. Pick up the mother wavelet $\psi$. The implemented CWT of the signal y is then denoted as a $N \times n_a$ matrix $W_y$.

Step 2. Different reallocation rules, denoted as $\omega_y$, are implemented for different NTFA technique. In synchrosqueezing transform (SST), it is implemented as a $N \times n_a$ matrix $\omega_y$ by the following entry-wise calculation:

$$\omega_y = \frac{-i \partial_b W_y(i,j)}{2\pi W_y(i,j)} \text{ when } W_y(i,j) \neq 0, \text{ or} \tag{3}$$

$$\omega_y = -\infty \text{ when } W_y(i,j) = 0.$$

where $\partial_b W_y$ is a $N \times n_a$ matrix coming from finite difference of $W_y$ with related to time.

Step 3. The final TFR of y is implemented. Discretize the frequency domain $$\left[\frac{1}{N\tau}, \frac{1}{2\tau}\right]$$

by equally spaced intervals of length $$\Delta_\xi = \frac{1}{N\tau}.$$

Here, $$\frac{1}{N\tau} \text{ and } \frac{1}{2\tau}$$

are the minimal and maximal frequencies detectable by the Fourier transform theorem. Denote $$n_\xi = \left[\frac{\frac{1}{2\tau} - \frac{1}{N\tau}}{\Delta_\xi}\right],$$

which is the number of the discretization of the frequency axis. Fix $\Gamma>0$, the NTFA of y, denoted by a $N \times n_\xi$ matrix $S_y$, is evaluated by reallocating the CWT coefficients. If $S_y$ is defined as $$S_y(i,j) = \sum_{\substack{k: |\omega_y(i,k) - j\Delta_\xi| \le \Delta_\xi/2, \\ |W_y(i,j)| \ge \Gamma}} \frac{\log(2)\sqrt{a_j}}{\Delta_\xi n_v} W_y(i,k) \quad (4)$$

where $i=1, \ldots, N$ and $j=1, \ldots, n_\xi$, the NTFA is called the SST.

A discretized curve $c^* \in Z_{n_\xi}^N$, where $Z_{n_\xi}=\{1, \ldots, n_\xi\}$ indexes the discretized frequency axis, to the dominant area of $S_y$ by:

$$c^* := \operatorname{argmax}_{c \in Z_{n_\xi}^N} \sum_{m=1}^N \log\left(\frac{|S_y(m, c(m))|}{\sum_{i=1}^{n_\xi}\sum_{j=1}^N |S_y(j,i)|}\right) - \lambda \sum_{m=2}^N |c_m - c_{m-1}|^2 \quad (5)$$

where $\lambda > 0$ determining the regularity of the estimated curve. Denote the maximizer of the functional in equation (5) as $c^* \in \mathbb{R}^N$.

Then, several different kinds of features are extracted from y. For example, $$\varphi'(n) := c^*(n)\Delta_\xi \quad (6)$$

where $n=1, \ldots, N$, or $$A(n) := \left|\frac{2}{\mathcal{R}_\psi}\Delta_\xi \sum_{i=c^*(n)-\lfloor\Delta/\Delta_\xi\rfloor}^{c^*(n)+\lfloor\Delta/\Delta_\xi\rfloor} S_Y(n,i)\right| \quad (7)$$

where $n=1, \ldots, N$. Here, $\varphi'(n)$ is the estimated IF an $A(n)$ is the estimated AM at time in.

Figure 2:
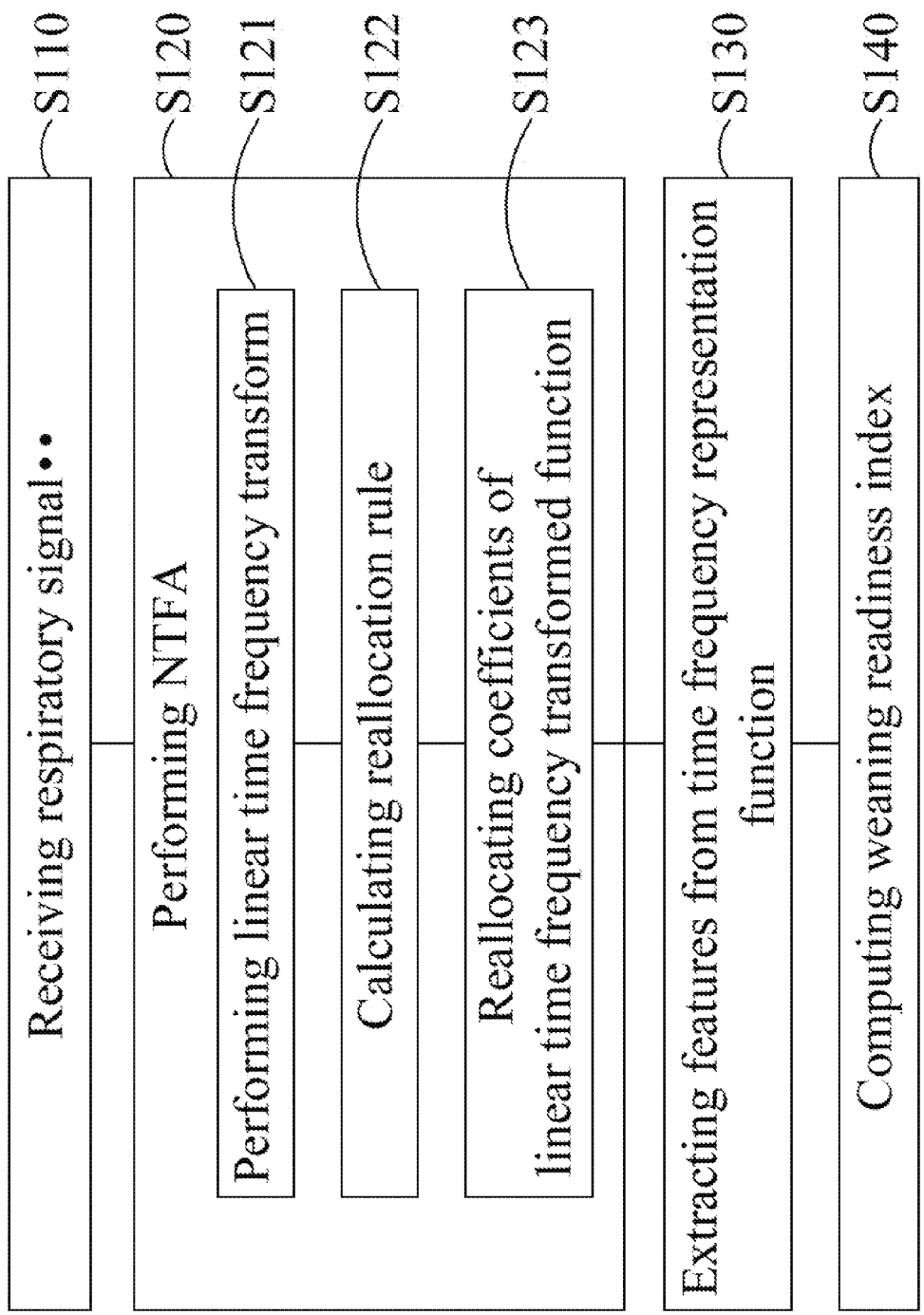
FIG. 2 illustrates a flowchart of an algorithm for the weaning readiness indicator shown in FIG. 1.

Please refer to FIG. 2, which is a flowchart of an algorithm for the weaning readiness indicator shown in FIG. 1. The aforementioned steps of algorithm of the embodiment in accordance with the present invention can be concluded by FIG. 2. In step S110, the monitor 20 monitors the respiratory signal from the patient 10 and sends the monitored respiratory signal to the processor 30. In steps S120-S140, the processor 30 implements the algorithm prestored in the memory 40. First, in step S120, the processor 30 performs NTFA on the received respiratory signal. The step S120 can be further split into 3 sub-steps S121, S122, and S123. In sub-step S121, the processor performs a linear time frequency transform on the respiratory signal, and obtains the linear time frequency transformed function. In sub-step S122, the processor calculates a reallocation rule according to the linear time frequency transformed function. In sub-step S123, the processor calculates the reallocating coefficients of the linear time frequency transformed function, and obtains the TFR function. Subsequently, in step S130, the features, such as IF and AM, are extracted from the TFR function. In step S140, the processor calculates the weaning readiness index based on the extracted features.

Preferably, the instantaneous frequency may be generated by a casual reassignment method (CRM). The CRM is one of the NTFA techniques.

To reduce the numerical error and noise influence, the casual reassignment method (CRM) can be used. In particular, the CRM may include a temporal reassignment rule and a frequency reassignment rule. Given a function f in the proper space, for example a tempered distribution, the STFT associated with a window function h(t) can be defined as:

$$V_f^{(h)}(t,\eta) := \int f(s)h(s-t)e^{-i2\pi\eta(s-t)}ds \quad (8)$$

where $t \in \mathbb{R}$ is the time, $\eta \in \mathbb{R}^+$ is the frequency, and h is a chosen window function, which is usually a Gaussian function with kernel bandwidth $\sigma > 0$.

Then, the reassignment rules, denoted as $\gamma_f$ and $\Omega_f$, are given in every points (t, $\omega$) by:

$$\Upsilon_f^{(h,\Gamma)}(t,\omega) = \begin{cases} \mathcal{R}\frac{V_f^{(\mathcal{T}h)}(t,\eta)}{V_f^{(h)}(t,\eta)} & \text{when } |V_f^{(h)}(t,\eta)| > \Gamma \\ \infty & \text{when } |V_f^{(h)}(t,\eta)| \le \Gamma \end{cases} \quad (9)$$

$$\Omega_f^{(h,\Gamma)}(t,\omega) = \begin{cases} -\mathcal{J}\frac{V_f^{(\mathcal{D}h)}(t,\eta)}{V_f^{(h)}(t,\eta)} & \text{when } |V_f^{(h)}(t,\eta)| > \Gamma \\ \infty & \text{when } |V_f^{(h)}(t,\eta)| \le \Gamma \end{cases} \quad (10)$$

where $\Gamma>0$ is the chosen hard threshold to reduce the numerical error and noise influence, $\mathcal{T}h(t)=t \cdot h(t)$ and $\mathcal{D}h=h'$, the first derivative of h. Here $\gamma_f$ is called as the temporal reassignment rule and $\Omega_f$ is called as the frequency reassignment rule. The CRM is defined as moving the STFT coefficient $V_f^{(h)}(s,\eta)$, at time s and frequency $\eta$ to a new time and frequency slot:

$$R_f^{(h,\Gamma,\alpha)}(t,\xi) := \int_{I_{\text{in}}} V_f^{(h)}(s,\eta)g_\alpha(|t-\Upsilon_f^{(h)}(s,\eta)|)g_\alpha(|\xi-\Omega_f^{(h)}(s,\eta)|)dsd\eta \quad (11)$$

where $I_{\text{in}} := \{(s,\eta): s<0+\sigma, |V_f^{(h)}(s,\eta)|>\Gamma\}$, $0<\alpha\ll1$ is chosen by the user.

$$g_\alpha(*) := \frac{1}{\alpha}g\left(\frac{*}{\alpha}\right),$$

g is a smooth function so that $g_\alpha \to \delta$ in the weak sense as $\alpha \to 0$. With CRM, a better instantaneous IF can be obtained. With this obtained IF as an estimator, the AM can be reconstructed from the NTFA result as well. The obtained IF and AM would serve as features for weaning readiness index to achieve better weaning success prediction.

To stabilize the presentation determined by the CRM, the multi-taper technique was introduced in the literature for the reassignment and NTFA. Given J orthonormal windows $h_j$, j=1, ..., J, one determines the reassignment rules as well as the corresponding CRM $R_f^{(h_j,\Gamma,\alpha)}(t,\xi)$. Then, the multi-taper casual reassignment method (MTCRM) is defined:

$$MR_f^{\Gamma,\alpha}(t,\xi) := \frac{1}{J}\sum_{j=1}^{J} R_f^{(h_j,\Gamma,\alpha)}(t,\xi) \qquad (12)$$

The third feature would be the concentration of the time frequency representation determined by MTCRM at each time, called the time-varying shape index. Denote the concentration at time t as c(t). The concentration indices are defined as the mean and standard deviation of c(t), denoted as M and S. The respiratory system dynamics is nonlinear and not easy to get a global picture by one parameter. How the signal oscillates for each oscillation, which is called the shape, is one aspect of the nonlinear dynamics. This variation of the shape could be obtained from reading the time frequency representation provided by the NTFA. Indeed, it is mainly represented by how the concentration of the time frequency representation distributed. The time varying concentration pattern measured by the skewness is called the time-varying shape index, which is regarded as one index representing the dynamics.

The estimated IF and AM are used to determine the weaning readiness index. In particular, the variance generated from IF and AM can be used as the weaning index (WIN). However, the present invention is not limited thereto, and other functions or indexes calculated from the IF and AM can be used to obtain the WIN as well. The following is an embodiment applying the variance:

$$WIN = \text{var}\left(\frac{AM(t)}{IF(t)}\right) \qquad (13)$$

With other analysis (e.g., receiver operating characteristic (ROC) curve analysis) and machine learning, the cut-off value of WIN can be determined. The cut-off value of WIN is used to separate a majority of patients with success weaning procedure from those with failure weaning procedure. Therefore, this cut-off value of WIN can help physicians to make decision if a patient is ready for weaning from mechanical ventilator.

Preferably, the predetermined time length may be less than 5 minutes.

Due to the property of NTFA, the required observation time of respiratory signal can be significantly reduced. In particular, the predetermined time length for capturing the respiratory can be shortened to 5 minutes. In some embodiments, the predetermined time length for capturing the respiratory signal can be shortened to 3 minute, and the final reliability for success weaning is still equal to or even better than the traditional RSBI method.

On the preliminary dataset, with the time-varying shape index, the accuracy increases from 76% to 82%, with the confidence interval [0.7, 0.89]. The threshold depends on the chosen scale, and could be rescaled to be 88.88.

The monitor 20 used in the weaning index indicator can be the device disposed with the ventilator wore by the patient 10. In particular, the monitor 20 may be a pneumotachometer, a turbine pneumotach, or an ultrasonic spirometer. Therefore, the monitor 20 can detect the air flow from the breathing of the patient 10 and generate the respiratory signal accordingly.

Figure 3:
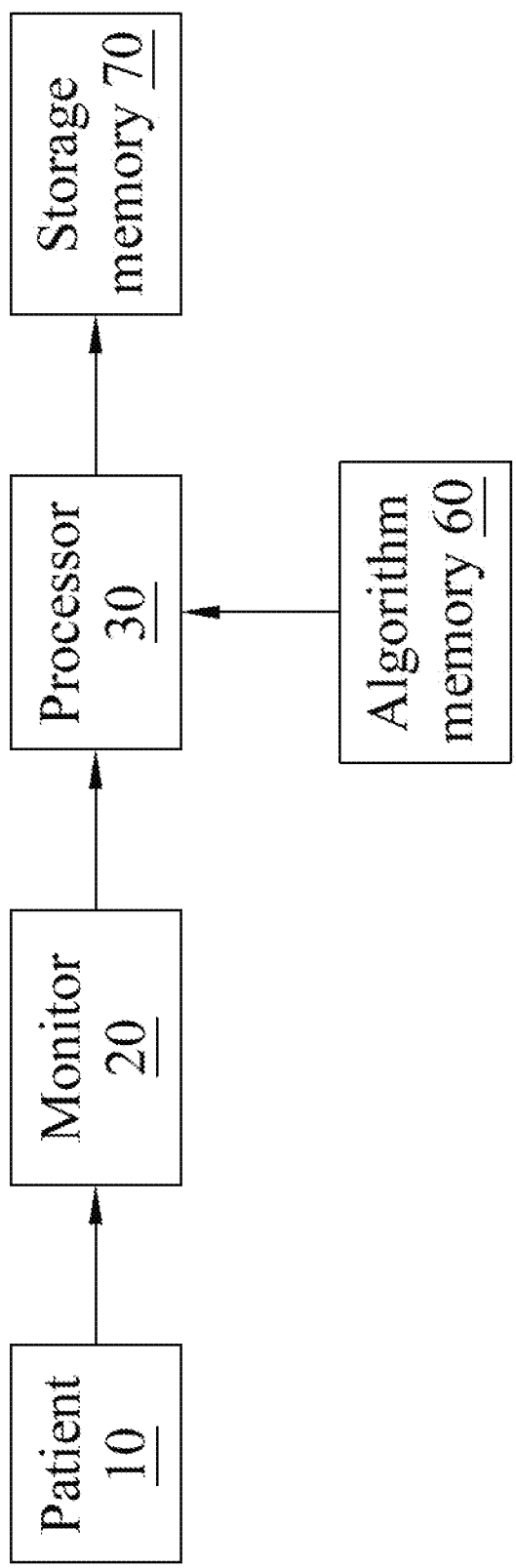
FIG. 3 illustrates a schematic diagram of a sleeping status recording device in accordance with a second embodiment of the present invention.

Please refer to FIG. 3, which is a schematic diagram of a sleeping status recording device in accordance with a second embodiment of the present invention. In FIG. 3, a sleeping status recording device is shown. The sleeping status recording device includes a monitor 20, an algorithm memory 60, a processor 30, and a storage memory 70. The monitor 20 monitors a sleeping patient 10 and generating a respiratory signal and an electrocardiography signal. The algorithm memory 60 stores an algorithm, where the algorithm includes performing a NTFA on the respiratory signal and an R-peak to R-peak interval signal extracted from the electrocardiography signal to obtain TFR functions respectively, extracting one or more features from the TFR functions, and determining a sleeping status based on the one or more features. The processor 30 is connected to the monitor 20 and the algorithm memory 60 and executes the algorithm to obtain the sleeping status. The storage memory 70 is connected to the processor 30 and stores the sleeping status.

Similar to the weaning application, the algorithm of NTFA can be used in the application of sleeping treatment. In particular, physicians usually have to diagnose the patients with sleeping issues by analyzing the sleeping status of the patients. Hence, how to evaluate the sleeping status becomes an import subject for the medical treatment. Comparing with the traditional methods, the index indicating the sleeping status generated by the NTFA can provide better insight for the patient. For example, the aforementioned IF and AM generated by NTFA can be applied to indicate distinct sleeping stages (e.g., REM, N1, N2, and N3). The definition of the sleeping stages can be stored in the algorithm memory 60 in advance and the method of calculating and evaluating the sleeping stage can be further modified by machine learning techniques. Support vector machine (SVM) is a commonly used technique for the purpose of classification statistical learning theory for machine learning. After the sleeping stages and status of the patient are calculated, the storage memory 70 can store the final result. Therefore, the physician can easily understand the whole history of the patient's sleeping, and provide the appropriate medical treatment accordingly.

Since the process of obtaining the IF and AM is similar to the weaning readiness indicator provided in the embodiment above in accordance with the present invention, the detailed calculation and algorithm are omitted here.

In addition to IF and AM generated by from the SST function, the sleeping status recording device of the embodiment in accordance with the present invention can also apply other index generated from other algorithm to evaluate the sleeping stages. In particular, the sleeping status recording device can apply an R-peak to R-peak interval signal extracted from the electrocardiography signal to obtain a time frequency representation. The feature extracted from the time frequency representation comprises an instantaneous frequency, an amplitude modulation and a coupling index. To quantify the physiological dynamics is via the integrated activity among different systems. A common approach is studying the coupling between the heart rate variability and the respiration. The coupling could be defined by reading the similarity between the time frequency representation of the R peak to R peak interval time series and the respiratory signal. With this quantified coupling, the time-varying index could be defined by the distance between these two time frequency representations. Therefore, the overall accuracy of sleeping status determination can be further improved.

Figure 4:
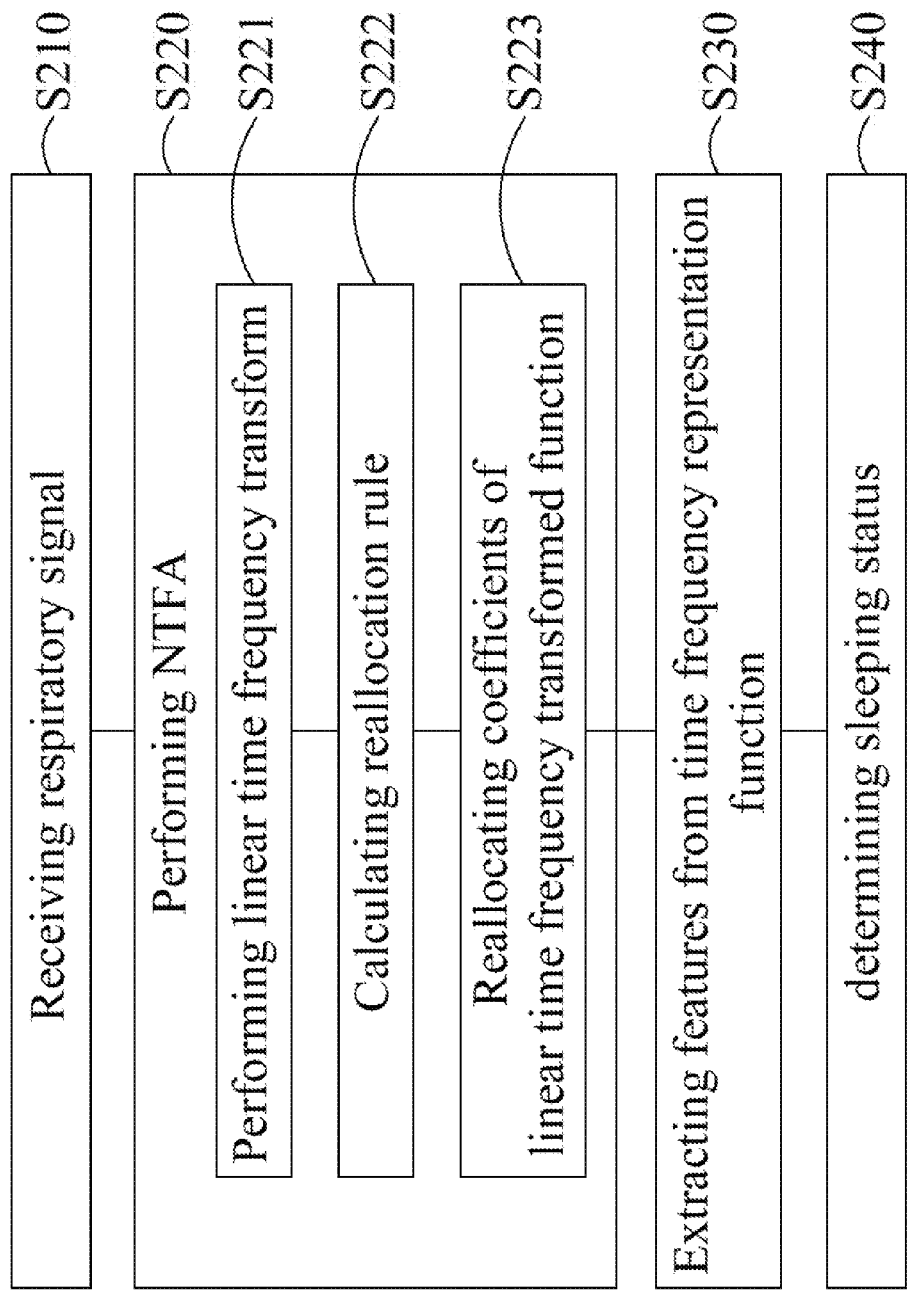
FIG. 4 illustrates a flowchart of an algorithm for the sleeping status recording device shown in FIG. 3.

Please refer to FIG. 4, which is a flowchart of an algorithm for the sleeping status recording device shown in FIG. 3. In this embodiment, steps S210-S230 generally correspond to steps S110-S130 described in the previous embodiment, and thus the description is omitted here. Finally, in step S240, the processor determines the sleeping status according to the features extracted from the TFR function.

The monitor may be an ECG machine, a pneumotachometer, a turbine pneumotach, an ultrasonic spirometer, a magnetometer, or a strain gauge.

As described above, the monitor 20 can directly detect the airflow of the patient's breathing and generates the respiratory signal. Such examples are described in the first embodiment and the detailed description is omitted here. In addition, for the patient with sleeping issue but without ventilator, there is a relatively gentle way to obtain the respiratory. That is, the respiratory signal can be generated by detecting the chest wall movement of the patient. In that case, the monitor 20 may be a magnetometer or a strain gauge. The magnetometer or the strain gauge may be disposed around the chest of the patient. When the patient breathes, the chest of the patient shifts and causes the measurement unit of the magnetometer moves or applies pressure to the strain gauge. Therefore, the magnetometer or the strain gauge can detect the respiratory signal of the patient without the ventilator or directly detecting the airflow generated from the patient.

Figure 5:
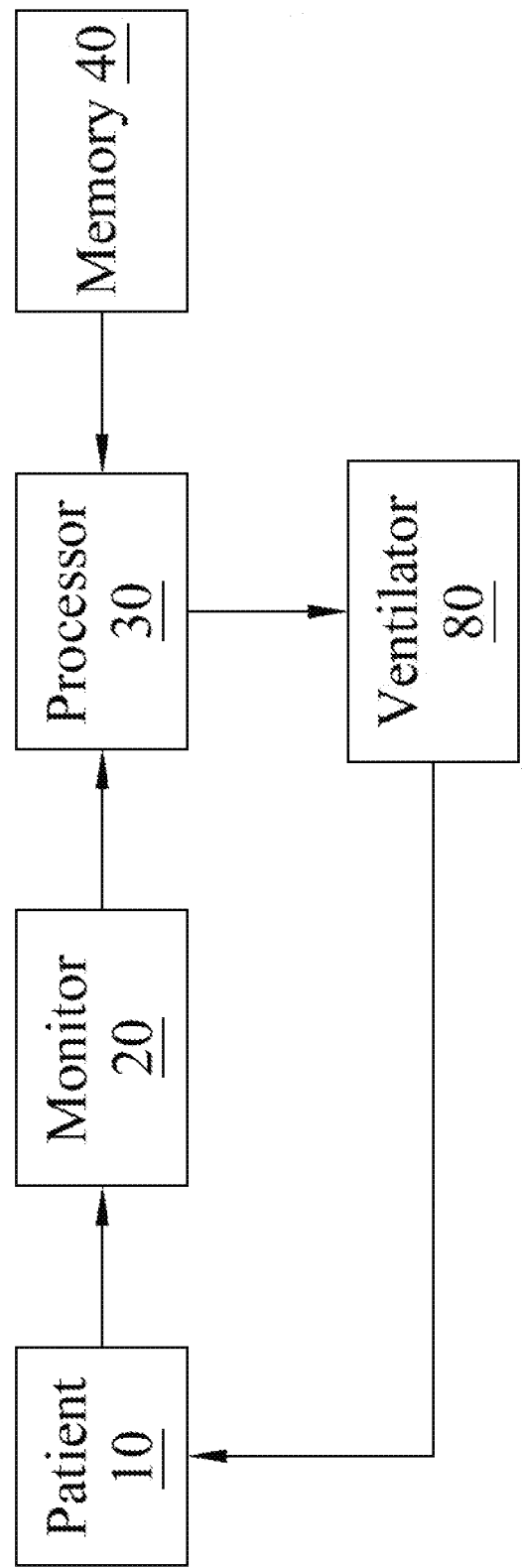
FIG. 5 illustrates a schematic diagram of an air providing system in accordance with a third embodiment of the present invention.

Please refer to FIG. 5, which is a schematic diagram of an air providing system in accordance with a third embodiment of the present invention. In FIG. 5, an air providing system is provided. The air providing system includes a monitor 20, a memory 40, a processor 30, and a ventilator 80. The monitor 20 monitors a patient 10 for a predetermined time length and generates a respiratory signal. The memory 40 stores an algorithm, where the algorithm includes performing a NTFA on the respiratory signal to obtain a TFR function, extracting one or more features from the synchrosqueezing transformed function, and computing a respiratory state indication of the patient based on the one or more features. The processor 30 is connected to the monitor 20 and the memory 40, and executes the algorithm. The ventilator 80 is connected to the processor 30 and provides air to the patient 10 according to the respiratory state indication.

In addition to provide the weaning index for reference to the physician, the algorithm of NTFA can be used to automatically adjust the air providing parameters of the ventilator 80. If the breathing status of the patient 10 has rapid variation in a short period, the ventilator 80 can immediately response to such variation and select appreciate air providing parameters for the patient 10 according to the respiratory state indication calculated by the processor 30. Therefore, the risk of missing effective timing for the occurrence of emergency may be reduced. In some embodiment, the adjustable air providing parameters may be the oxygen concentration or the total pressure. However, the present invention is not limited thereto. Other parameters may be adjusted as well.

In particular, the respiratory state indication provided to the ventilator 80 is generated by the aforementioned TFR function. As described above, one of the properties of the NTFA algorithm is that it can extract effective features even when the observed signal is short (e.g., the observed respiratory signal can only have 3 minute length). Hence, when the breathing status of the patient 10 rapidly changes, the air providing system of the embodiment of the present invention can easily make an immediate response. Since commonly used methods, such as RSBI, may need longer respiratory signal to extract effective features, the response time of the air providing system applying them may be significantly longer. Therefore, the air providing system of the embodiment in accordance with the present invention provides a better solution to treat emergency case.

In addition, the ventilator 80 may be a continuous positive airway pressure (CPAP) ventilator. The CPAP is used to treat the patient with Obstructive Sleep Apnea (OSA). The CPAP can provide different pressure to eliminate the respiratory disorders and snoring, and effectively reduce the respiratory disturbance index (like AHI, RDI). When the patient 10 changes their sleeping status, the breathing status may also change. Thus, the monitor 20 monitors the patient 10 for generating the respiratory signal during the sleeping status. The processor 30 computes the respiratory state for determined time interval. The respiratory state indication is sent to the CPAP ventilator and the pressure provided by the CPAP ventilator is changed correspondingly. The adjustable ventilator may provide more comfortable experience for the patient 10.

While the means of specific embodiments in present disclosure has been described by reference drawings, numerous modifications and variations could be made thereto by those skilled in the art without departing from the scope and spirit of the invention set forth in the claims. The modifications and variations should in a range limited by the specification of the present invention.

What is claimed is:

1. A weaning readiness indicator, comprising:
   a monitor monitoring a ventilated patient for a predetermined time length and generating a respiratory signal;
   a memory storing an algorithm, wherein the algorithm comprises performing a nonlinear time frequency analysis on the respiratory signal to obtain a time frequency representation function, extracting one or more features from the time frequency representation function, and computing a weaning readiness index based on the one or more features;
   a processor connected to the monitor and the memory, and executing the algorithm; and
   a display connected to the processor and providing an indication of the weaning readiness index of the ventilated patient,
   wherein the features comprise an instantaneous frequency, an amplitude modulation and a time varying shape index, and the instantaneous frequency is generated by a casual reassignment method with a temporal reassignment rule and a frequency reassignment rule, and
   wherein in the algorithm, the step of performing the nonlinear time frequency analysis on the respiratory signal to obtain the time frequency representation function further comprises performing a linear time frequency transform on the respiratory signal to obtain a linear time frequency transformed function, calculating a reallocation rule from the linear time frequency transformed function, and reallocating coefficients of the linear time frequency transformed function based on the reallocation rule to obtain the time frequency representation function.

2. The weaning readiness indicator as claimed in claim 1, wherein the instantaneous frequency, the amplitude modulation and the time varying shape index are generated by a casual reassignment method.

3. The weaning readiness indicator as claimed in claim 1, wherein the linear time frequency transform comprises a short time Fourier transform and a continuous wavelet transform.

4. The weaning readiness indicator as claimed in claim 1, wherein the predetermined time length is less than 5 minutes.

5. The weaning readiness indicator as claimed in claim 1, wherein the monitor comprises a pneumotachometer, a turbine pneumotach, or an ultrasonic spirometer.

* * * * *